(12) United States Patent
Voegele

(10) Patent No.: US 8,081,810 B2
(45) Date of Patent: Dec. 20, 2011

(54) RECOGNIZING A REAL WORLD FIDUCIAL IN IMAGE DATA OF A PATIENT

(75) Inventor: James W. Voegele, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 880 days.

(21) Appl. No.: 11/726,653

(22) Filed: Mar. 22, 2007

(65) Prior Publication Data

US 2008/0232656 A1  Sep. 25, 2008

(51) Int. Cl.
*G06K 9/00* (2006.01)

(52) U.S. Cl. ....................................................... 382/131

(58) Field of Classification Search .................. 382/128, 382/131, 151, 190, 203, 291, 306; 378/20, 378/68; 600/373
See application file for complete search history.

(56) References Cited

U.S. PATENT DOCUMENTS

| | | | |
|---|---|---|---|
| 5,391,199 A | 2/1995 | Ben-Haim | |
| 5,398,691 A | 3/1995 | Martin | |
| 5,497,934 A | 3/1996 | Brady et al. | |
| 5,575,288 A | 11/1996 | Sliwa | |
| 5,636,255 A * | 6/1997 | Ellis | 378/20 |
| 5,728,044 A | 3/1998 | Shan | |
| 5,729,129 A | 3/1998 | Acker | |
| 5,771,896 A | 6/1998 | Sliwa | |
| 5,772,594 A * | 6/1998 | Barrick | 600/407 |
| 5,836,869 A | 11/1998 | Kudo et al. | |
| 5,868,673 A | 2/1999 | Vesely | |
| 6,016,439 A * | 1/2000 | Acker | 600/411 |
| 6,092,526 A | 7/2000 | LaFontaine et al. | |
| 6,167,292 A | 12/2000 | Badano et al. | |
| 6,252,599 B1 | 6/2001 | Natsuko et al. | |
| 6,321,106 B1 | 11/2001 | Lemelson | |
| 6,381,485 B1 * | 4/2002 | Hunter et al. | 600/407 |
| 6,428,547 B1 | 8/2002 | Vilsmeier | |
| 6,456,735 B1 | 9/2002 | Sato et al. | |
| 6,491,702 B2 | 12/2002 | Heilbrun et al. | |

(Continued)

FOREIGN PATENT DOCUMENTS

| | | |
|---|---|---|
| DE | 102005022901 | 11/2006 |
| EP | 0920838 | 6/1999 |
| EP | 1410758 | 4/2004 |
| EP | 1652470 | 5/2006 |
| FR | 2779339 | 12/1999 |

OTHER PUBLICATIONS

EP, Supplementary European Search Report, European Application No. 08730689.0; 6 pages (Apr. 28, 2010).

(Continued)

*Primary Examiner* — Jason M Repko
*Assistant Examiner* — Shervin Nakhjavan

(57) ABSTRACT

A storage medium contains a program which instructs a computer to recognize a predetermined shape of each of at least one portion of a medical assembly as a real-world fiducial in image data of a patient when the image data includes the predetermined shape and is received by the digital computer. The at-least-one portion has another function apart from functioning as a real-world fiducial. A medical apparatus includes a medical assembly and a storage medium. The medical assembly includes a component having at-least-one portion each with a predetermined shape. The storage medium contains a program which instructs a computer to recognize the predetermined shape of each of the at-least-one portion as a real-world fiducial in image data of a patient when the image data includes the predetermined shape and is received by the digital computer. The component has another function apart from functioning as a real-world fiducial.

16 Claims, 2 Drawing Sheets

U.S. PATENT DOCUMENTS

| | | | |
|---|---|---|---|
| 6,546,279 B1* | 4/2003 | Bova et al. | 600/429 |
| 6,556,695 B1* | 4/2003 | Packer et al. | 382/128 |
| 6,615,063 B1 | 9/2003 | Ntziachristos et al. | |
| 6,690,964 B2 | 2/2004 | Bieger et al. | |
| 6,773,402 B2 | 8/2004 | Govari et al. | |
| 7,366,562 B2 | 4/2008 | Dukesherer et al. | |
| 7,697,972 B2 | 4/2010 | Verard et al. | |
| 7,764,985 B2* | 7/2010 | McCombs et al. | 600/429 |
| 7,840,256 B2* | 11/2010 | Lakin et al. | 600/426 |
| 2001/0029333 A1 | 10/2001 | Shahidi | |
| 2001/0044578 A1* | 11/2001 | Ben-Haim et al. | 600/424 |
| 2002/0007108 A1 | 1/2002 | Chen et al. | |
| 2002/0087101 A1* | 7/2002 | Barrick et al. | 600/587 |
| 2002/0156363 A1 | 10/2002 | Hunter et al. | |
| 2003/0065294 A1 | 4/2003 | Pickup et al. | |
| 2003/0139668 A1 | 7/2003 | Ben-Haim et al. | |
| 2003/0160721 A1 | 8/2003 | Gilboa et al. | |
| 2004/0101822 A1 | 5/2004 | Wiesner et al. | |
| 2004/0105979 A1 | 6/2004 | Bayless | |
| 2004/0167391 A1* | 8/2004 | Solar et al. | 600/411 |
| 2005/0020878 A1 | 1/2005 | Ohnishi et al. | |
| 2005/0020918 A1 | 1/2005 | Wilk et al. | |
| 2005/0033164 A1 | 2/2005 | Yatsuo et al. | |
| 2005/0080333 A1 | 4/2005 | Piron et al. | |
| 2005/0085793 A1 | 4/2005 | Glossop | |
| 2005/0152836 A1 | 7/2005 | Ashley et al. | |
| 2005/0182295 A1 | 8/2005 | Soper et al. | |
| 2005/0196028 A1 | 9/2005 | Kleen et al. | |
| 2005/0203420 A1 | 9/2005 | Kleen et al. | |
| 2006/0052701 A1 | 3/2006 | Carter | |
| 2006/0058644 A1* | 3/2006 | Hoppe et al. | 600/423 |
| 2006/0064006 A1 | 3/2006 | Strommer et al. | |
| 2006/0089624 A1 | 4/2006 | Voegele et al. | |
| 2006/0089625 A1 | 4/2006 | Voegele et al. | |
| 2006/0089626 A1 | 4/2006 | Voegele et al. | |
| 2006/0142657 A1 | 6/2006 | Quaid et al. | |
| 2006/0149134 A1 | 7/2006 | Soper et al. | |
| 2006/0173299 A1 | 8/2006 | Romley et al. | |
| 2006/0183246 A1 | 8/2006 | Wiesner et al. | |
| 2006/0239544 A1 | 10/2006 | Yankelevitz et al. | |
| 2006/0245971 A1 | 11/2006 | Burns et al. | |
| 2006/0271056 A1 | 11/2006 | Terrill-Grisoni et al. | |
| 2007/0147705 A1 | 6/2007 | Clune et al. | |
| 2007/0173689 A1 | 7/2007 | Ozaki et al. | |
| 2007/0191707 A1* | 8/2007 | Denittis | 600/424 |
| 2007/0270685 A1 | 11/2007 | Kang et al. | |
| 2008/0086051 A1 | 4/2008 | Voegele | |
| 2008/0118103 A1 | 5/2008 | Pescatore et al. | |
| 2008/0221434 A1 | 9/2008 | Voegele | |
| 2008/0234544 A1 | 9/2008 | Voegele | |
| 2008/0234566 A1 | 9/2008 | Voegele et al. | |
| 2008/0234720 A1* | 9/2008 | Chang et al. | 606/196 |
| 2008/0298655 A1* | 12/2008 | Edwards | 382/128 |
| 2008/0319307 A1 | 12/2008 | Voegele et al. | |
| 2009/0054761 A1 | 2/2009 | Voegele et al. | |
| 2009/0161927 A1 | 6/2009 | Mori et al. | |

OTHER PUBLICATIONS

PCT, International Preliminary Report on Patentability, International Application No. PCT/US2008/056043; 5 pages (Sep. 15, 2009).
PCT, International Preliminary Report on Patentability, International Application No. PCT/US2008/057323; 5 pages (Sep. 22, 2009).
PCT, International Preliminary Report on Patentability, International Application No. PCT/US2008/057322; 5 pages (Sep. 22, 2009).
PCT, International Preliminary Report on Patentability, International Application No. PCT/US2007/078832; 6 pages (Mar. 24, 2009).
PCT, International Preliminary Report on Patentability, International Application No. PCT/US2008/054933; 6 pages (Sep. 8, 2009).
US, Office Action, U.S. Appl. No. 11/716,465; 15 pages (Jun. 24, 2009).
US, Office Action, U.S. Appl. No. 11/716,465; 11 pages (Mar. 16, 2010).
US, Office Action, U.S. Appl. No. 11/524,216; 21 pages (Aug. 19, 2008).
US, Office Action, U.S. Appl. No. 11/524,216; 20 pages (Jan. 22, 2009).
US, Advisory Action, U.S. Appl. No. 11/524,216; 3 pages (Apr. 15, 2009).
US, Office Action, U.S. Appl. No. 11/524,216; 19 pages (Jun. 23, 2009).
US, Office Action, U.S. Appl. No. 11/524,216; 16 pages (Mar. 3, 2010).
US, Advisory Action, U.S. Appl. No. 11/524,216; 3 pages (May 11, 2010).
US, Office Action, U.S. Appl. No. 11/726,257; 17 pages (Aug. 6, 2009).
US, Office Action, U.S. Appl. No. 11/726,257; 16 pages (Mar. 2, 2010).
Invitrogen—Qdot In Vivo Imaging, 2006 Introgen Corporation, 5 pages, webpage.
Kodak—Kodak X-Sight Imaging Agent for In Vivo Applications, 2007, 3 pages, Webpage.
Hybrid Silica Technologies, Inc.—01. Hybrid Silica Technologies, Inc. (HST) Founded to Commercialize CU Dots Fluorescent Nanoparticles, 2004, by the Office of the Vice Provost for Research, Cornell University, 2 pages, Webpage.
CN, Notification of First Office Action, Chinese Application No. 200780034771.0 (Aug. 11, 2010).
CN, Notification of First Office Action, Chinese Application No. 200880012795.0 (Oct. 20, 2010).
EP, Office Action, European Application No. 07842741.6 (Oct. 12, 2010).
EP, Search Report, European Application No. 08743996.4 (Apr. 8, 2011).
US, Office Action, U.S. Appl. No. 11/725,834 (Mar. 22, 2011).
US, Office Action, U.S. Appl. No. 11/894,841 (Feb. 25, 2011).
US, Office Action, U.S. Appl. No. 11/894,841 (Nov. 3, 2010).
EP, Supplementary European Search Report, European Application No. 08743996.4 (Apr. 8, 2011).
EP, Decision to Grant, European Application No. 08730689.0 (Apr. 21, 2011).
PCT, International Preliminary Report on Patentability, International Application No. PCT/US2008/056043 (Sep. 15, 2009).
PCT, International Preliminary Report on Patentability, International Application No. PCT/US2008/054933 (Sep. 8, 2009).
PCT, International Preliminary Report on Patentability, International Application No. PCT/US2007/078832 (Mar. 24, 2009).
PCT, International Preliminary Report on Patentability, International Application No. PCT/US2008/057323 (Sep. 22, 2009).
PCT, International Preliminary Report on Patentability, International Application No. PCT/US2008/057322 (Sep. 22, 2009).
US, Office Action, U.S. Appl. No. 11/820,354 (Jun. 29, 2011).
Supplementary Partial European Search Report, European Patent Application No. 07842741 (8 pages) (Aug. 6, 2009).
International Search Report, International Application No. PCT/US2008/054933 (3 pages) (mailed Aug. 20, 2008; published Nov. 27, 2008).
International Search Report, International Application No. PCT/US2007/078832 (2 pages) (mailed Apr. 10, 2008; published Jul. 3, 2008).
Viergever, M.A. et al., "Integration of functional and anatomical brain images," *Biophy. Chem.*, vol. 68, pp. 207-219 (1997).
PCT, International Search Report, PCT/US08/57323 (Aug. 7, 2008).
PCT, International Search Report, PCT/US08/57322 (Aug. 18, 2008).
PCT, International Search Report, PCT/US08/56043 (Aug. 26, 2008).
Supplementary Partial European Search Report, European Application No. 07842741.6 (8 pages) (Aug. 6, 2009).
U.S. Appl. No. 11/524,216, filed Apr. 2008, Voegele, James W.
Website document of Mimics Software from Materialise (8 pages), Jun. 2007.
US, Office Action, U.S. Appl. No. 11/725,834 (Aug. 1, 2011).

* cited by examiner

RECOGNIZING A REAL WORLD FIDUCIAL IN IMAGE DATA OF A PATIENT

FIELD OF THE INVENTION

The present invention is related generally to medical images, and more particularly to a storage medium containing a computer program and to medical apparatus including a medical assembly and a storage medium containing a computer program all relating to recognizing a real world fiducial in image data of a patient.

BACKGROUND OF THE INVENTION

Imagers are known for obtaining image data of a patient and for displaying images of the image data on a display monitor. Such images include, without limitation, ultrasound images, X-ray images, computerized tomography (CT) images, positive electron emission (PET) images, magnetic resonance (MRI) images, fluoroscope images, etc. Where needed, it is known to register these images with a real world object by placing a marker on the skin of the patient, wherein the marker has a predetermined shape, and wherein the marker is recognizable in the image data using pattern recognition software (e.g., a conventional segmentation subroutine).

Position sensors are known which are placed on medical instruments which are inserted into a patient allowing the position of the medical instrument to be tracked inside the patient. Such position sensors are part of known position sensing systems such as an AC-based system available from Biosense-Webster or a DC-based system available from Ascension Technology Corporation.

Still, scientists and engineers continue to seek improvements in recognizing a real world fiducial in image data of a patient.

SUMMARY

A first expression of an embodiment of the invention is for a storage medium containing a program readable by a digital computer which instructs the digital computer to recognize a predetermined shape of each of at least one portion of a medical assembly as a real-world fiducial in image data of a patient when the image data includes the predetermined shape and is received as an input by the digital computer. The at-least-one portion has another function apart from functioning as a real-world fiducial.

A second expression of an embodiment of the invention is for medical apparatus including a medical assembly and a storage medium. The medical assembly includes a component having at-least-one portion each with a predetermined shape. The storage medium contains a program readable by a digital computer which instructs the digital computer to recognize the predetermined shape of each of the at-least-one portion as a real-world fiducial in image data of a patient when the image data includes the predetermined shape and is received as an input by the digital computer. The component has another function apart from functioning as a real-world fiducial.

Several benefits and advantages are obtained from one or more expressions of the embodiment of the invention. In one example of registering an image of a patient with a real world object, the need for a separate marker having no function apart from being a real-world fiducial is eliminated. In the same or a different example, the portion of the medical assembly serving as a real-world fiducial is insertable (i.e., capable of being inserted) into the patient, instead of being conventionally placed on the skin of the patient, allowing for less image data to be generated, for some medical procedures, in order for at least some image data to contain the real-world fiducial.

DETAILED DESCRIPTION

Before explaining the embodiment of the present invention in detail, it should be noted that the present invention is not limited in its application or use to the details of construction and arrangement of parts and steps illustrated in the accompanying drawings and description. The illustrative embodiment of the invention may be implemented or incorporated in other embodiments, methods, variations and modifications, and may be practiced or carried out in various ways. Furthermore, unless otherwise indicated, the terms and expressions employed herein have been chosen for the purpose of describing the illustrative embodiment of the present invention for the convenience of the reader and are not for the purpose of limiting the invention.

It is further understood that any one or more of the following-described implementations, examples etc. can be combined with any one or more of the other following-described implementations, examples etc.

Figure 1:
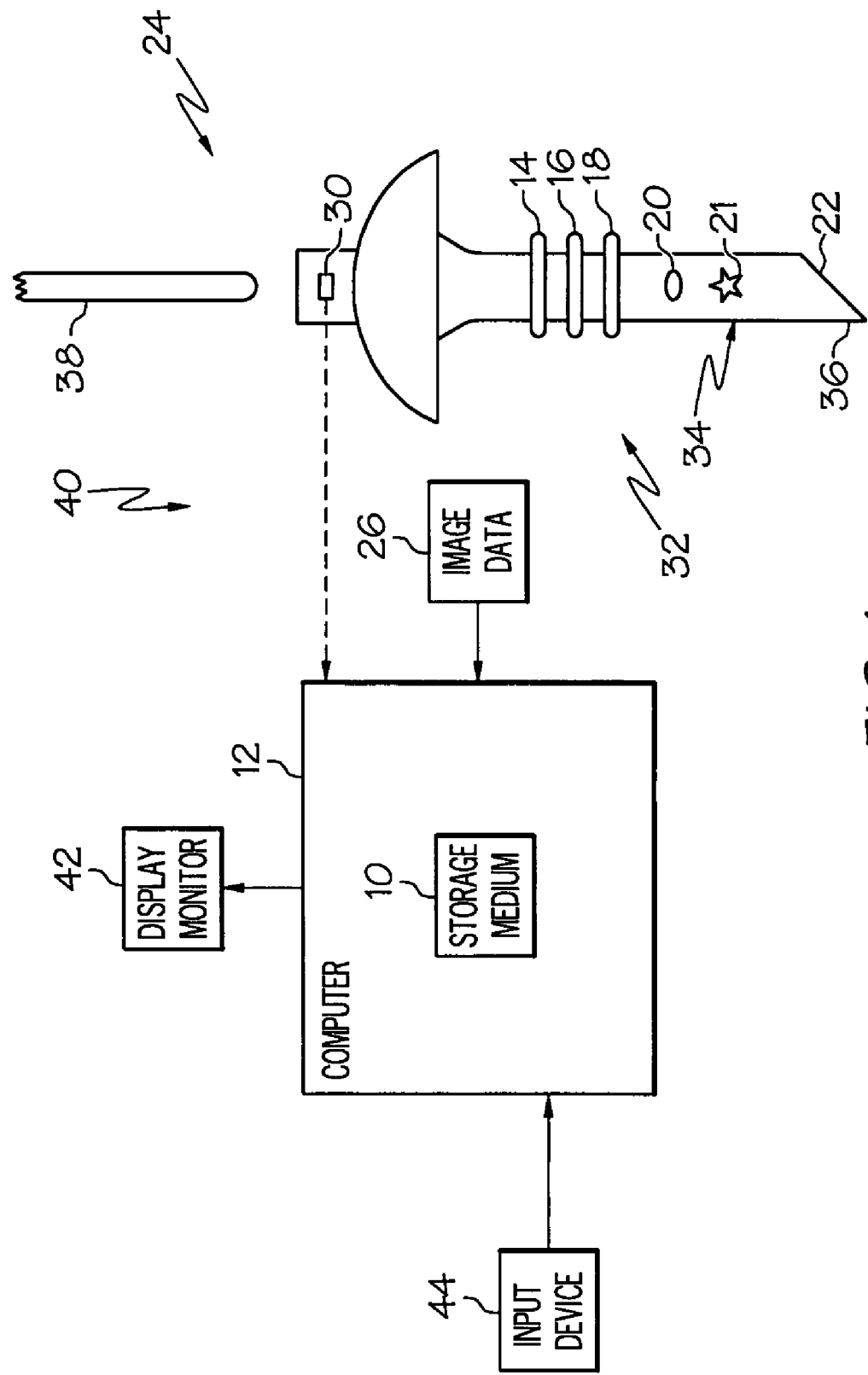
FIG. 1 is a schematic view of an embodiment of the invention showing a digital computer and an example of a medical assembly, wherein the digital computer includes a storage medium, wherein the medical assembly example includes a component and an ablation probe, and wherein the component functions as an insertion sleeve and also functions as at least one real-world fiducial in image data of the patient.
Figure 2:
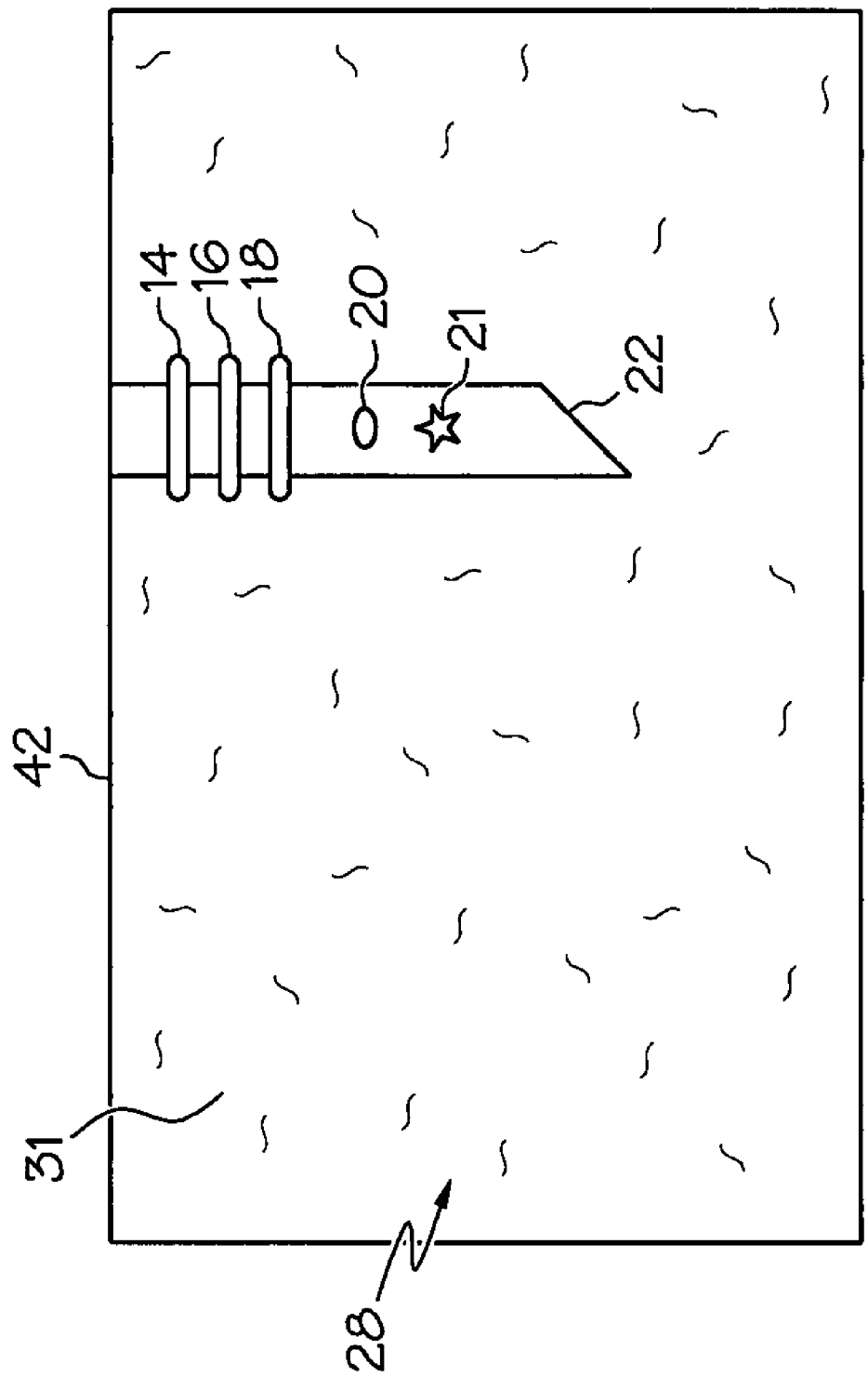
FIG. 2 is a schematic view of a display monitor upon which the digital computer displays an image of the image data.

An embodiment of the invention is shown in FIGS. 1-2. A first expression of the embodiment of FIGS. 1-2 is for a storage medium 10 containing a program readable by a digital computer 12 which instructs the digital computer 12 to recognize a predetermined shape of each of at least one portion 14, 16, 18, 20 and 22 of a medical assembly 24 as a real-world fiducial in image data 26 of a patient 28 when the image data 26 includes the predetermined shape and is received as an input by the digital computer 12. The at-least-one portion 14, 16, 18, 20 and 22 has another function apart from functioning as a real-world fiducial. It is noted that the words "at least one portion" includes "the entirety", and that the term "assembly" includes, without limitation, "component". In one example, the program includes a conventional segmentation subroutine to identify the predetermined shape.

Examples of storage media include, without limitation, temporary computer memory and permanent computer memory such as RAM, hard drives, CD's, etc. Examples of image data 26 include, without limitation, ultrasound image data, X-ray image data, computerized tomography (CT) image data, positive electron emission (PET) image data, magnetic resonance (MRI) image data, and fluoroscope image data. An example of a computer program which creates a manipulative 3D display image from 2D CT-scans and MRI-scans is Mimics available from Materialise of Ann Arbor, Mich. It is noted that the image data 26 may be pre-acquired image data or real-time image data. In one arrangement, the predetermined shape is a shape recognizable as a "manufactured" shape as opposed to biological shapes occurring in image data of a patient.

In one implementation of the first expression of the embodiment of FIGS. 1-2, the medical assembly 24 includes a (wired or wireless) position sensor 30 adapted to provide position data, and each at-least-one portion 14, 16, 18, 20 and 22 is located at a predetermined position with respect to the position sensor 30. In one variation, the at-least-one portion 14, 16, 18, 20 and 22 is adapted to have a fixed position relative to the patient 28 during a medical treatment of the patient 28. In one modification, the program instructs the digital computer 12 to perform steps a) through c). Step a) includes calculating a position of the position sensor using at least position data obtained from the position sensor and indexed to a reference coordinate system. Step b) includes creating an image representation using at least the image data obtained from the patient and indexed to the reference coordinate system using at least the recognized predetermined shape, the predetermined position, and the indexed position of the position sensor. Step c) includes displaying an image of the image representation.

In one realization of the first expression of the embodiment of FIGS. 1-2, the position data and/or the image data 26 are already indexed to the reference coordinate system when received by the computer 12. In a different realization, the position data and/or the image data 26 are not yet indexed to the reference coordinate system when received by the computer 12, and such indexing is performed by the computer 12.

Examples of position sensors 30 adapted to provide position data include, without limitation, the position sensors of the AC-based position sensing system available from Biosense-Webster and the DC-based position sensing system available from Ascension Technology Corporation. It is noted that, as used in describing the system embodiment of FIGS. 1-2, the term "position" includes up to six degrees of freedom so that calculating position includes calculating a two dimensional or three-dimensional translation and two or three degrees of orientation of the sensor 30 with respect to a reference coordinate system. A description of the operation of an embodiment of a position sensor 30 adapted to provide position data is found in US Patent Application Publication 2006/0089624.

In one illustration of the first expression of the system embodiment of FIGS. 1-2, the sensor 30 is considered to be a position sensor of a Biosense Webster positioning sensing system and a transmitter, not shown, of such system is used by the digital computer 12 for a reference coordinate system for position data from the position sensor 30. Thus, the digital computer 12 can index the position data of the sensor 30 to a reference coordinate system. The position of the at-least-one portion 14, 16, 18, 20 and 22 is predetermined with respect to the position sensor 30. Thus the position of the at-least-one portion 14, 16, 18, 20 and 22 is related to the reference coordinate system. Since the image data 26 is related to the predetermined shape of each of the at-least-one portion 14, 16, 18, 20 and 22, a subroutine can be written by those of ordinary skill in the art, without undue experimentation, which instructs the digital computer 12 to create the image representation of the image data 26 indexed to the reference coordinate system.

In one application of the first expression of the embodiment of FIGS. 1-2, the at-least-one portion 14, 16, 18, 20 and 22 includes a plurality of portions 14, 16 and 18 each having a same shape. In the same or a different application, the at-least-one portion 14, 16, 18, 20 and 22 includes a plurality of portions 14, 20 and 22 each having a different shape.

In one enablement of the first expression of the embodiment of FIGS. 1-2, the medical assembly 24 includes an insertion sleeve 34 insertable into the patient 28, and the at-least-one portion 14, 16, 18, 20 and 22 is at-least-one portion (such as a patient-insertable portion) of the insertion sleeve 34. In one illustration, the at-least-one portion 14, 16, 18, 20 and 22 is chosen from the group consisting of an external rib 14, 16 and 18 of the insertion sleeve 34 and a distal hole 22 of a distal end 36 of the insertion sleeve 34. In one variation, the medical treatment assembly includes a surgical device 38 insertable into the patient 28 through the insertion sleeve 34. It is noted that the term "device" includes, without limitation, "component". In one modification, the surgical device 36 is an ablation probe. In a different example, not shown, the component is a holder for a medical diagnostic and/or medical treatment device.

In this enablement, the position sensor 30 is the only sensor of the medical assembly 24 which is attached to the insertion sleeve 34 and adapted to provide position data. In one variation, the position sensor 30 is attached to a patient-non-insertable portion of the insertion sleeve 34. It is noted that the position sensor 30 may be temporarily attached or permanently attached to the insertion sleeve 34, wherein "temporarily attached" means the position sensor may be detached from the insertion sleeve without damage to the position sensor and/or the insertion sleeve and wherein "permanently attached" means the position sensor may not be detached from the insertion sleeve without damage to the position sensor and/or the insertion sleeve. In a different variation, not shown, the position sensor is attached to a patient-insertable portion of the insertion sleeve 34. In a further variation, not shown, the position sensor is attached to orthopaedic hardware of the patient 28.

A first method of the invention is a method for visualizing a patient 28 and comprises steps a) through e). Step a) includes obtaining a medical assembly 24 having at least one portion 14, 16, 18, 20 and 22 each with a predetermined shape adapted for recognition as a real-world fiducial in image data 26 of the patient 28, wherein the at-least-one portion 14, 16, 18, 20 and 22 has another function apart from functioning as a real-world fiducial. Step b) includes disposing the medical assembly 24 with the at-least-one portion 14, 16, 18, 20 and 22 on or in the patient 28. Step c) includes obtaining the image data 26 of the patient 28. Step d) includes recognizing the at-least-one portion 14, 16, 18, 20 and 22 in the image data 26. Step e) includes displaying an image 31 of the image data 26 which includes the at-least-one portion 14, 16, 18, 20 and 22.

A second expression of an embodiment of the invention is for medical apparatus 40 including a medical assembly 24 and a storage medium 10. The medical assembly 24 includes a component (e.g., insertion sleeve 34) having at-least-one portion 14, 16, 18, 20 and 22 each with a predetermined shape. The storage medium 10 contains a program readable by a digital computer 12 which instructs the digital computer 12 to recognize the predetermined shape of each of the at-least-one portion 14, 16, 18, 20 and 22 as a real-world fiducial in image data 26 of a patient 28 when the image data 26 includes the predetermined shape and is received as an input by the digital computer 12. The component (e.g., insertion sleeve 34) has another function apart from functioning as a real-world fiducial.

It is noted that the implementations, examples, etc. of the first expression of the embodiment of FIGS. 1-2 are equally applicable to the second expression of the embodiment of FIGS. 1-2. In a further illustration of the second expression of the embodiment of FIGS. 1-2, the group from which the at-least-one portion 14, 16, 18, 20 and 22 is chosen also consists of a side hole 20 created in the insertion sleeve 34 and a raised or recessed symbol 21 created or disposed on the insertion sleeve 34. It is noted that symbols includes letters and numbers as well as non-alphanumeric symbols such as a five-pointed star, etc. The symbols are distinguishable in the image 31 due to a different mass density relative to their surroundings.

A second method of the invention is a method for visualizing a patient 28 and comprises steps a) through e). Step a) includes obtaining a medical assembly 24 including a component (e.g., insertion sleeve 34) having at least one portion 14, 16, 18, 20 and 22 each with a predetermined shape adapted for recognition as a real-world fiducial in image data 26 of the patient 28, wherein the component (e.g., insertion sleeve 34) has another function apart from functioning as a real-world fiducial. Step b) includes disposing the medical assembly 24 with the at-least-one portion 14, 16, 18, 20 and 22 of the component (e.g., insertion sleeve 34) on or in the patient 28. Step c) includes obtaining the image data 26 of the patient 28. Step d) includes recognizing the at-least-one portion 14, 16, 18, 20 and 22 in the image data 26. Step e) includes displaying an image 31 of the image data 26 which includes the at-least-one portion 14, 16, 18, 20 and 22.

In one variation of either or both of the methods, the medical assembly 24 includes a position sensor 30 and each at-least-one portion 14, 16, 18, 20 and 22 is located at a predetermined position with respect to the position sensor 30. In one modification, the at-least-one portion 14, 16, 18, 20 and 22 is adapted to have a fixed position relative to the patient during a medical treatment of the patient 28. In one example, there is also included, between steps d) and e) the step of indexing the image data 26 to a reference coordinate system using a position sensor 30 and in a manner as previously discussed.

In a first extension of either or both of the expressions of the embodiment of FIGS. 1-2, there is also included a display monitor 42 upon which the image 31 is displayed. Examples of a display monitor 42 include, without limitation, a computer monitor, a goggle display screen, and a room wall upon which projected images are displayed.

In an employment of either or both of the expressions of the embodiment of FIGS. 1-2, the image 31 is a three-dimensional manipulative image, and there is also included a computer input device 44 operatively connected to the digital computer 12 to allow a user to manipulate the three-dimensional-manipulative image on the display monitor 42. Examples of input devices 44 include, without limitation, a keyboard and a mouse. In a different employment, the image is a two-dimensional non-manipulative image.

Several benefits and advantages are obtained from one or more expressions of the embodiment of the invention. In one example of registering an image of a patient with a real world object, the need for a separate marker having no function apart from being a real-world fiducial is eliminated. In the same or a different example, the portion of the medical assembly serving as a real-world fiducial is insertable (i.e., capable of being inserted) into the patient, instead of being conventionally placed on the skin of the patient, allowing for less image data to be generated, for some medical procedures, in order for at least some image data to contain the real-world fiducial.

While the present invention has been illustrated by expressions of an embodiment and enablements, applications, etc. thereof, it is not the intention of the applicant to restrict or limit the spirit and scope of the appended claims to such detail. Numerous other variations, changes, and substitutions will occur to those skilled in the art without departing from the scope of the invention. It will be understood that the foregoing description is provided by way of example, and that other modifications may occur to those skilled in the art without departing from the scope and spirit of the appended Claims.

What is claimed is:

1. A non-transitory storage medium containing a program readable by a digital computer which instructs the digital computer to recognize a predetermined shape of each of at least one portion of a medical assembly as a real-world fiducial in image data of a patient when the image data includes the predetermined shape and is received as an input by the digital computer, wherein the at-least-one portion has another function apart from functioning as a real-world fiducial, wherein the medical assembly includes a position sensor adapted to provide position data and wherein each of the at-least-one portion is located at a fixed, predetermined position with respect to the position sensor such that the real-world fiducial is fixed in position relative to the position sensor, wherein the medical assembly includes an insertion sleeve insertable into the patient through which a surgical device is inserted into the patient for a medical treatment of the patient and wherein the at-least-one portion is at-least-one portion of the insertion sleeve.

2. The storage medium of claim 1, wherein the at-least-one portion is adapted to have a fixed position relative to the patient during the medical treatment of the patient.

3. The storage medium of claim 2, wherein the program instructs the digital computer to calculate a position of the position sensor using at least position data obtained from the position sensor and indexed to a reference coordinate system, to create an image representation using at least the image data obtained from the patient and indexed to the reference coordinate system using at least the recognized predetermined shape, the predetermined position, and the indexed position of the position sensor, and to display an image of the image representation.

4. The storage medium of claim 1, wherein the at-least-one portion includes a plurality of portions each having a same shape.

5. The storage medium of claim 1, wherein the at-least-one portion includes a plurality of portions each having a different shape.

6. The storage medium of claim 1, wherein the at-least-one portion is chosen from the group consisting of an external rib of the insertion sleeve and a distal hole of a distal end of the insertion sleeve and the at-least-one portion is recognized by the digital computer based upon the predetermined shape.

7. The storage medium of claim 6, wherein the medical assembly includes the surgical device insertable into the patient through the insertion sleeve and wherein the surgical device is a medical treatment device.

8. The storage medium of claim 7, wherein the surgical device is an ablation probe.

9. Medical apparatus comprising a medical assembly and a storage medium, wherein the medical assembly includes a component having at-least-one portion each with a predetermined shape, wherein the storage medium contains a program readable by a digital computer which instructs the digital computer to recognize the predetermined shape of each of the at-least-one portion as a real-world fiducial in image data of a patient when the image data includes the predetermined shape and is received as an input by the digital computer, and wherein the at-least-one portion has another function apart from functioning as a real-world fiducial, wherein the medical assembly includes a position sensor adapted to provide position data and wherein each at-least-one portion is located at a fixed, predetermined position with respect to the position sensor such that the real-world fiducial is fixed relative to the position sensor and wherein the medical assembly includes an insertion sleeve insertable into the patient through which a surgical device is inserted into the patient for a medical treatment of the patient and wherein the at-least-one portion is at-least-one portion of the insertion sleeve.

10. The medical apparatus of claim 9, wherein the at-least-one portion is adapted to have a fixed position relative to the patient during the medical treatment of the patient.

11. The medical apparatus of claim 10, wherein the program instructs the digital computer to calculate a position of the position sensor using at least position data obtained from the position sensor and indexed to a reference coordinate system, to create an image representation using at least the image data obtained from the patient and indexed to the reference coordinate system using at least the recognized predetermined shape, the predetermined position, and the indexed position of the position sensor, and to display an image of the image representation.

12. The medical apparatus of claim 9, wherein the at-least-one portion includes a plurality of portions each having a same shape.

13. The medical apparatus of claim 9, wherein the at-least-one portion includes a plurality of portions each having a different shape.

14. The medical apparatus of claim 9, wherein the at-least-one portion is chosen from the group consisting of an external rib of the insertion sleeve, a distal hole of a distal end of the insertion sleeve, a side hole created in the insertion sleeve, and a raised or recessed symbol created on the insertion sleeve and the at-least-one portion is recognized by the digital computer based upon the predetermined shape.

15. The medical apparatus of claim 14, wherein the medical assembly includes a surgical device insertable into the patient through the insertion sleeve and wherein the surgical device is a medical treatment device.

16. The medical apparatus of claim 15, wherein the surgical device is an ablation probe.

* * * * *